(12) United States Patent
Georgescu et al.

(10) Patent No.: US 11,514,571 B2
(45) Date of Patent: Nov. 29, 2022

(54) HIERARCHICAL ANALYSIS OF MEDICAL IMAGES FOR IDENTIFYING AND ASSESSING LYMPH NODES

(71) Applicant: Siemens Healthcare GmbH, Erlangen (DE)

(72) Inventors: Bogdan Georgescu, Princeton, NJ (US); Elijah D. Bolluyt, Easton, PA (US); Alexandra Comaniciu, Princeton Junction, NJ (US); Sasa Grbic, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 157 days.

(21) Appl. No.: 16/714,031

(22) Filed: Dec. 13, 2019

(65) Prior Publication Data
US 2020/0193594 A1    Jun. 18, 2020

Related U.S. Application Data

(60) Provisional application No. 62/780,577, filed on Dec. 17, 2018.

(51) Int. Cl.
*G06T 7/11* (2017.01)
*G06T 7/00* (2017.01)
(Continued)

(52) U.S. Cl.
CPC ............ *G06T 7/0012* (2013.01); *A61B 5/418* (2013.01); *G06T 7/11* (2017.01); *G06T 11/008* (2013.01);
(Continued)

(58) Field of Classification Search
CPC .................. A61B 5/418; G06T 11/008; G06T 2207/10081; G06T 2207/20081;
(Continued)

(56) References Cited

U.S. PATENT DOCUMENTS

| 7,447,359 | B2 * | 11/2008 | Tu ........................ G06K 9/6256 382/173 |
| 7,804,990 | B2 * | 9/2010 | Kiraly ....................... G06T 7/73 382/128 |

(Continued)

OTHER PUBLICATIONS

Barbu et al., "Automatic Detection and Segmentation of Lymph Nodes from CT Data", IEEE Transactions on Medical Imaging, Feb. 2012, vol. 31, No. 2, pp. 240-250.
(Continued)

*Primary Examiner* — Tsung Yin Tsai (57) ABSTRACT

Systems and methods for identifying and assessing lymph nodes are provided. Medical image data (e.g., one or more computed tomography images) of a patient is received and anatomical landmarks in the medical image data are detected. Anatomical objects are segmented from the medical image data based on the one or more detected anatomical landmarks. Lymph nodes are identified in the medical image data based on the one or more detected anatomical landmarks and the one or more segmented anatomical objects. The identified lymph nodes may be assessed by segmenting the identified lymph nodes from the medical image data and quantifying the segmented lymph nodes. The identified lymph nodes and/or the assessment of the identified lymph nodes are output.

14 Claims, 5 Drawing Sheets

(51) Int. Cl.
    *G06T 11/00*     (2006.01)
    *A61B 5/00*      (2006.01)
(52) U.S. Cl.
    CPC ............... *G06T 2207/10081* (2013.01); *G06T 2207/20081* (2013.01); *G06T 2207/20084* (2013.01); *G06T 2207/20101* (2013.01); *G06T 2207/20112* (2013.01)
(58) Field of Classification Search
    CPC . G06T 2207/20084; G06T 2207/20101; G06T 2207/20112; G06T 2207/30096; G06T 7/0012; G06T 7/11
    See application file for complete search history.

(56) References Cited

U.S. PATENT DOCUMENTS

| | | | | |
|---|---|---|---|---|
| 8,073,220 | B2 | 12/2011 | Khamene et al. | |
| 9,589,374 | B1* | 3/2017 | Gao | A61B 6/5211 |
| 9,792,531 | B2 | 10/2017 | Georgescu et al. | |
| 9,922,433 | B2* | 3/2018 | Schieke | G06V 10/764 |
| 10,062,014 | B2 | 8/2018 | Zhou et al. | |
| 10,970,829 | B2* | 4/2021 | Zheng | G06N 3/0454 |
| 10,973,486 | B2* | 4/2021 | Sjöstrand | A61B 6/467 |
| 2007/0237373 | A1* | 10/2007 | Kiraly | G06T 7/73 600/407 |
| 2011/0007954 | A1* | 1/2011 | Suehling | G06V 40/10 382/128 |
| 2011/0033522 | A1* | 2/2011 | Reinherz | A61K 9/5123 435/339.1 |
| 2012/0189176 | A1* | 7/2012 | Giger | G06T 19/20 382/128 |
| 2016/0350946 | A1* | 12/2016 | Schieke | A61B 5/0091 |
| 2018/0144828 | A1* | 5/2018 | Baker | G16H 30/40 |
| 2018/0260957 | A1* | 9/2018 | Yang | G06T 7/143 |
| 2019/0066281 | A1* | 2/2019 | Zheng | G06T 5/006 |
| 2019/0139216 | A1* | 5/2019 | Georgescu | G16H 30/40 |
| 2019/0209116 | A1* | 7/2019 | Sjöstrand | G06T 15/08 |
| 2020/0193594 | A1* | 6/2020 | Georgescu | G06T 7/11 |
| 2020/0311919 | A1* | 10/2020 | Grimmer | G06T 7/32 |

OTHER PUBLICATIONS

Feulner et al., "Lymph Node Detection and Segmentation in Chest CT Data Using Discriminative Learning and a Spatial Prior", Medical Image Analysis, 2013, vol. 17, pp. 254-270.
Liu et al., "Mediastinal Lymph Node Detection and Station Mapping on Chest CT Using Spatial Priors and Random Forest," Medical Physics, Jul. 2016, vol. 43, No. 7, pp. 4362-4374.
Roth et al., "A New 2.5D Representation for Lymph Node Detection Using Random Sets of Deep Convolutional Neural Network Observations," Medical Image Computing and Computer-Assisted Intervention, 2014, vol. 8673, pp. 520-527.
Ghesu et al., "Multi-Scale Deep Reinforcement Learning for Real-Time 3D-Landmark Detection in CT Scans," IEEE Transactions on Pattern Analysis and Machine Intelligence, 2017, 14 pgs.
Yang et al., "Automatic Liver Segmentation Using an Adversarial Image-to-Image Network," Medical Image Computing and Computer-Assisted Intervention, 2017, pp. 507-515.
Ronneberger et al., "U-Net Convolutional Networks for Biomedical Image Segmentation," Medical Image Computing and Computer-Assisted Intervention, 2015, vol. 9351, pp. 234-241.
Sudre et al., "Generalised Dice Overlap as a Deep Learning Loss Function for Highly Unbalanced Segmentations," Deep Learning in Medical Image Analysis, 2017, vol. 10553, pp. 240-248.
Keskar et al., "On Large-Batch Training for Deep Learning: Generalization Gap and Sharp Minima," International Conference on Learning Representations, 2017, 16 pgs.
"A New 2.5 D Representation for Lymph Node Detection in CT," retrieved online on Dec. 11, 2019, at https://wiki.cancerimagingarchive.net/display/Public/CT+Lymph+Nodes, 1 pg.

* cited by examiner

HIERARCHICAL ANALYSIS OF MEDICAL IMAGES FOR IDENTIFYING AND ASSESSING LYMPH NODES

CROSS-REFERENCE TO RELATED APPLICATIONS

This application claims the benefit of U.S. Provisional Application No. 62/780,577, filed Dec. 17, 2018, the disclosure of which is incorporated herein by reference in its entirety.

TECHNICAL FIELD

The present invention relates generally to the identifying and assessing lymph nodes, and more particularly to a hierarchical analysis of medical images for identifying and assessing lymph nodes.

BACKGROUND

Identification and assessment of lymph nodes in computed tomography (CT) scans is important for the diagnosis and staging of cancers such as lymphoma and other cancers that metastasize to the lymphatic system. Currently, identification and assessment of lymph nodes in CT scans is typically performed manually by a radiologist. However, the manual identification and assessment of lymph nodes in CT scans is a time consuming process due to the small size of lymph nodes, the low contrast of lymph nodes in the CT scans as compared to their surroundings, and the highly variable shape and size of lymph nodes. Conventional techniques for the automatic identification and assessment of lymph nodes in CT scans typically apply probabilistic boosting trees, random forests, or other variants of deep neural networks. However, such conventional techniques for the automatic identification and assessment of lymph nodes in CT scans are inaccurate and result in a high number of false positives with respect to the detection of lymph nodes.

BRIEF SUMMARY OF THE INVENTION

In accordance with one or more embodiments, systems and methods for identifying and assessing lymph nodes are provided. Medical image data (e.g., one or more computed tomography images) of a patient is received and anatomical landmarks in the medical image data are detected. Anatomical objects are segmented from the medical image data based on the one or more detected anatomical landmarks. Lymph nodes are identified in the medical image data based on the one or more detected anatomical landmarks and the one or more segmented anatomical objects. The identified lymph nodes may be assessed by segmenting the identified lymph nodes from the medical image data and quantifying the segmented lymph nodes. The identified lymph nodes and/or the assessment of the identified lymph nodes are output.

In one embodiment, the lymph nodes are identified using a machine learning network based on voxels of the medical image data labelled as corresponding to the one or more anatomical objects according to the segmenting. The lymph nodes are identified from voxels of the medical image data that are not labelled as corresponding to the one or more anatomical objects. The machine learning network may be a U-Net trained to map intensities of voxels of the medical image data as a Gaussian volume.

In one embodiment, the landmarks are detected using an agent trained with deep reinforcement learning and the anatomical objects are segmented using an adversarial deep image-to-image network.

These and other advantages of the invention will be apparent to those of ordinary skill in the art by reference to the following detailed description and the accompanying drawings.

DETAILED DESCRIPTION

The present invention generally relates to methods and systems for the hierarchical analysis of medical images for identifying and assessing lymph nodes. Embodiments of the present invention are described herein to give a visual understanding of such methods and systems for the hierarchical analysis of medical images for identifying and assessing lymph nodes. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Further, it should be understood that while the embodiments discussed herein may be discussed with respect to the identification and assessment of lymph nodes from medical images, the present invention is not so limited. Embodiments of the present invention may be applied for the identification and assessment of any object of interest from any type of image.

Various embodiments of the present invention provide for hierarchical analysis of medical images for identifying and/or assessing lymph nodes. The hierarchical analysis applies a combination of different artificial intelligence agents or algorithms to automatically identify anatomical landmarks in medical image data and use the identified anatomical landmarks as context to robustly identify and assess lymph nodes in the medical image data. Advantageously, embodiments of the present invention reduce the number of false positives of identified lymph nodes, thereby resulting in increased performance and robustness as compared to conventional techniques.

Figure 1:
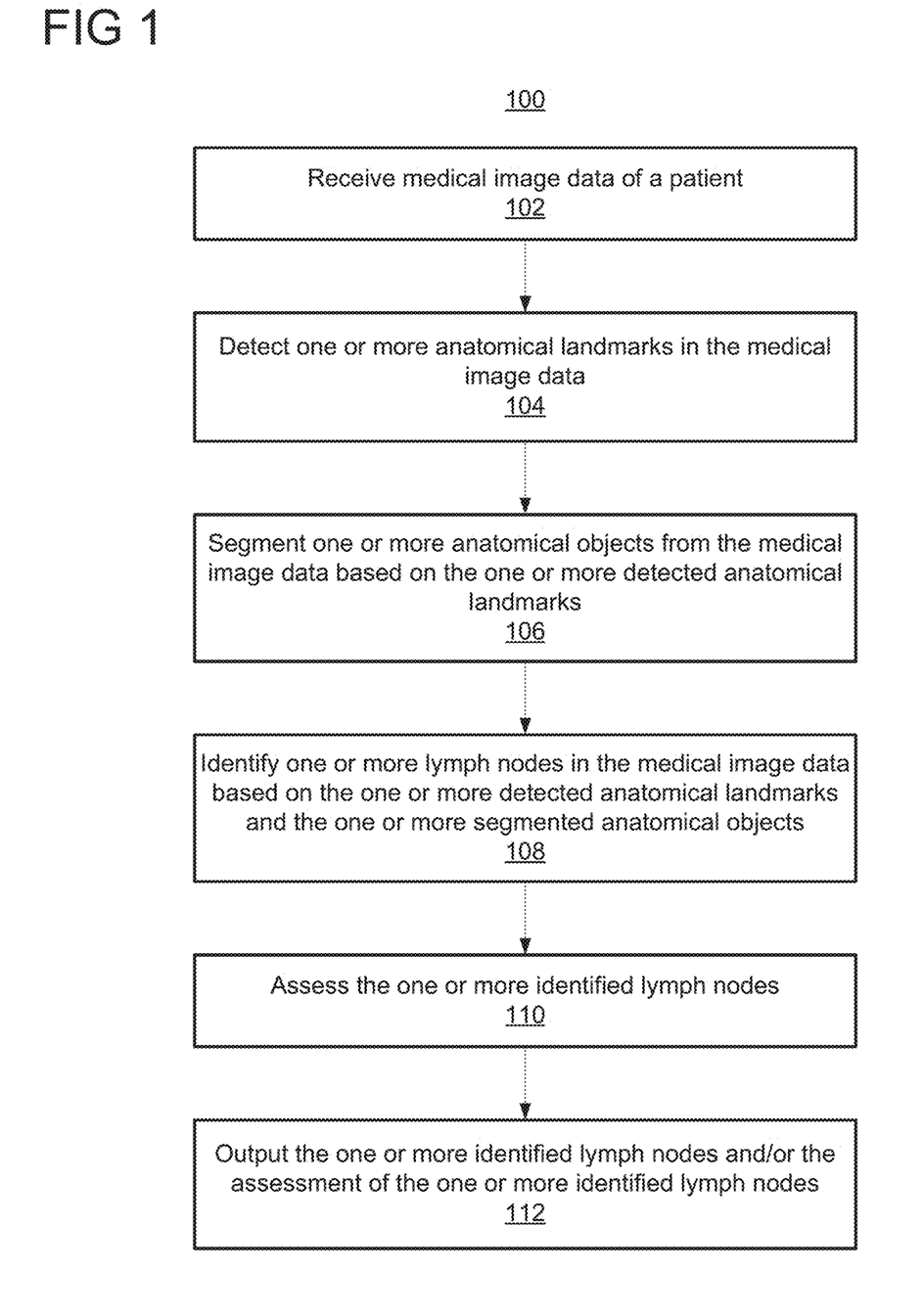
FIG. 1 shows a method for identifying and/or assessing lymph nodes in medical image data.

FIG. 1 shows a method 100 for identifying and/or assessing lymph nodes in medical image data, in accordance with one or more embodiments. Method 100 may be performed by any suitable computing device, such as, e.g., computer 502 of FIG. 5.

At step 102, medical image data of a patient is received. The medical image data may include one or more 2D or 3D medical images or volumes depicting one or more lymph nodes acquired in a scan of the patient. In one embodiment, the medical image data comprises a computed tomography (CT) scan, however it should be understood that the medical image data may be of any suitable modality, such as, e.g., x-ray, magnetic resonance imaging (MRI), ultrasound (US), single-photon emission computed tomography (SPECT), positron emission tomography (PET), or any other suitable modality or combination of modalities. The medical image data may be received directly from an image acquisition device, such as, e.g., image acquisition device 514 of FIG. 5 (e.g., a CT scanner, an MRI scanner, etc.), used to acquire the medical image data. Alternatively, the medical image data may be received by loading medical image data previously stored on a memory or storage of a computer system (e.g., a picture archiving and communication system, PACS) or by receiving medical image data via network transmission from a remote computer system.

At step 104, one or more anatomical landmarks are detected in the medical image data. Exemplary anatomical landmarks include anatomically meaningful locations on organs, bones, blood vessels, etc. The anatomical landmarks may be manually detected in the medical image data by a user (e.g., a clinician) or may be automatically detected in the medical image data by applying one or more computer-based automated detection algorithms to the medical image data.

Figure 2:
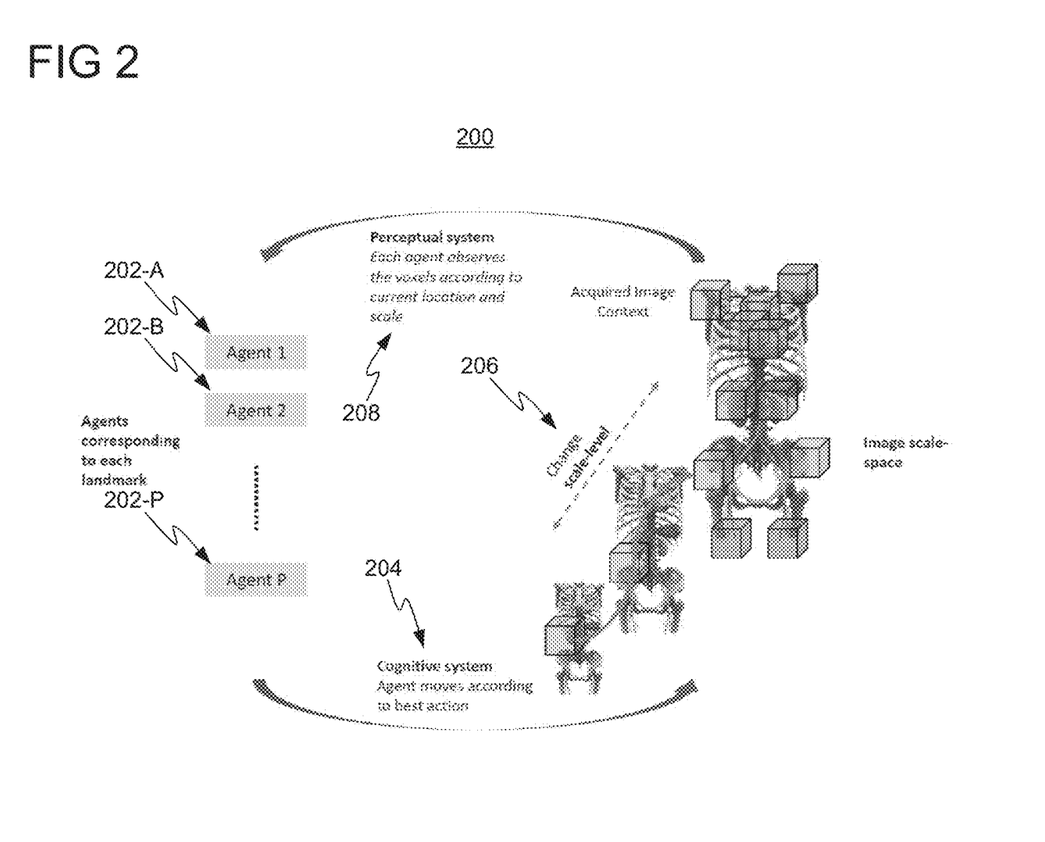
FIG. 2 shows a high-level framework for detecting anatomical landmarks in a medical image.

In one embodiment, the anatomical landmarks may be automatically detected in the medical image data using deep reinforcement learning. FIG. 2 shows a high-level framework 200 for detecting anatomical landmarks in a medical image using deep reinforcement learning. In framework 200, artificial intelligence agents 202-A, 202-B, . . . , 202-P (collectively referred to herein as agents 202) are taught how to iteratively navigate in the medical image to detect a corresponding target anatomical landmark. Agents 202 select from a set of actions that enables movement 204 across three dimensions of the medical image and movement 206 across image scales of the medical image from course to fine. Agents 202 observe 208 the voxels at their current location and scale and iteratively select from the set of actions based on the voxels. Agents 202 iteratively move in the medical image until the location of agents 202 converge to their target anatomical landmark, thereby providing the location of the target anatomical landmark. The output is a list of locations of the anatomical landmarks in a patient coordinate system. In some embodiments, the list of locations of the anatomical landmarks may be mapped to voxels in the medical image data. During training, agents 202 are taught the best sequence of actions through reinforcement learning by encouraging actions that move agents 202 closer to either the target anatomical landmark or outside of the medical image if the target anatomical landmark is not present. Agents 202 are modeled using a deep neural network that learns a mapping between voxel intensities at their current location to the probabilities of actions. Framework 200 has been evaluated on more than 2,500,000 CT images or 5,000 3D CT volumes from over 2,000 patients and achieved 0% false positive and false-negative rates at detecting if the anatomical landmarks are present in the field of view. Parsing one CT volume took approximately two seconds on average, thus enabling fast processing of large amounts of data. Further details of anatomical landmark detection using deep reinforcement learning are described in U.S. Pat. No. 9,792,531, entitled "Intelligent Multi-Scale Medical Image Landmark Detection," the disclosure of which is incorporated herein by reference in its entirety.

It should be understood that the present invention is not limited to the automatic detection of anatomical landmarks in the medical image data using deep reinforcement learning as described above, and that any other suitable technique for detecting anatomical landmarks in medical image data may be employed.

At step 106, one or more anatomical objects are segmented from the medical image data based on the one or more detected anatomical landmarks. The detected anatomical landmarks are used to trigger and define the segmentation. Exemplary anatomical objects include organs, bones, blood vessels, or any other suitable anatomical object. The anatomical objects may be automatically or semi-automatically segmented from the medical image data by applying one or more computer-based segmentation algorithms to the medical image data.

In one embodiment, the anatomical objects are automatically segmented from the medical image data using an adversarial deep image-to-image network. The adversarial deep image-to-image network comprises a generator network and a discriminator network. The generator network may be a deep image-to-image (DI2I) network that receives the medical image data and anatomical landmark locations (detected at step 104) as input and outputs a probability map indicating a probability score of voxels belonging to the anatomical objects. In one embodiment, the probability map may be converted to a binary segmentation mask by comparing the probability score to a threshold (e.g., 0.5) such that the binary segmentation mask has intensity values of 1 where the anatomical objects are located and 0 where the anatomical objects are not located. The generator network is a fully convolutional encoder-decoder architecture with dense blocks, multi-scale feature concatenation, and deep supervision. During training, the probability map or segmentation mask output by the generator network is input together with the ground truth probability map/segmentation mask to the discriminator network. The role of the discriminator network is to distinguish between the generated probability map/segmentation mask and the ground truth probability map/segmentation mask. The training is successful if the discriminator network cannot distinguish between the generated probability map/segmentation mask and the ground truth probability map/segmentation mask. An adversarial deep image-to-image network was trained to segment the following anatomical objects: all five lung lobes, airways, bone regions, ribs, spine, femur heads, brain, esophagus, heart, aorta, liver, spline, pancreas, bladder, prostate, rectum, left and right kidney, abdominal region, mediastinal region, and axillary region. The trained adversarial deep image-to-image network achieved a high accuracy with more than 0.95 DICE coefficient on average from the trained segmentations. Further details of automatic segmentation of anatomical objects from medical image data using an adversarial deep image-to-image network are described in U.S. Pat. No. 10,062,014, entitled "Deep Image-to-Image Network Learning for Medical Image Analysis," the disclosure of which is incorporated herein by reference in its entirety.

It should be understood that the present invention is not limited to the automatic segmentation of anatomical objects from medical image data using an adversarial deep image-to-image network as described above, and that any other suitable technique for segmenting anatomical objects from medical image data may be employed.

At step 108, one or more lymph nodes in the medical image data are identified based on the one or more detected anatomical landmarks and the one or more segmented anatomical objects. In particular, the lymph nodes are identified in various regions (e.g., axillary, mediastinal, and abdominal regions) based on image intensities and the context defined by the detected anatomical landmarks and the segmented anatomical objects. The lymph nodes The lymph nodes may be automatically identified in the medical image data by applying one or more computer-based automated detection algorithms to the medical image data.

Figure 3:
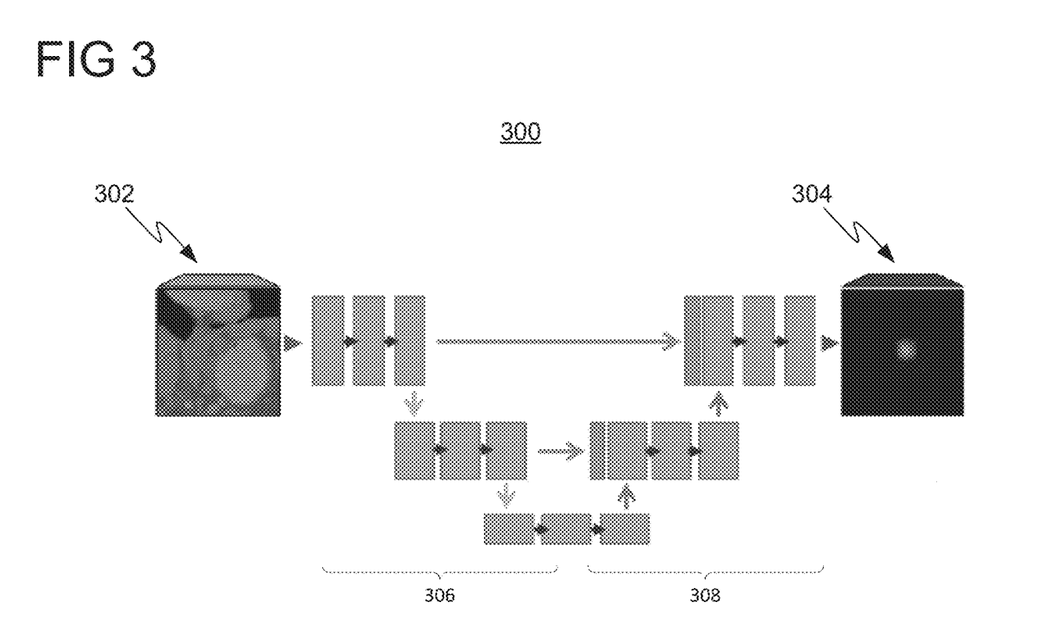
FIG. 3 shows a network architecture of a 3D U-Net.

In one embodiment, the lymph nodes may be identified in the medical image data using a U-Net. FIG. 3 shows a network architecture 300 of a 3D U-Net. Network architecture 300 of the U-Net comprises a contracting path 306 and an expansive path 308. Each box in contracting path 306 and expansive path 308 represents a multi-channel feature map. Contracting path 306 comprises the application of 3×3×3 convolutions each followed by a rectified linear unit (ReLU), represented as right arrows within contracting path 306 in FIG. 3, and 2×2×2 max pooling operation, represented as down arrows within contracting path 306 in FIG. 3. Expansive path 308 comprises application of 2×2×2 up convolutional operation, represented as up arrows within expansive path 308 in FIG. 3, followed by 2×2×2 convolutions each followed by a ReLU, represented as right arrows within expansive path 308 in FIG. 3. Arrows connecting layers from contracting path 306 to expansive path 308 represent skip connections.

The U-Net is able to learn deep hierarchical features while maintaining fine spatial details by the use of the skip connections, which is important due to the small size of the lymph nodes to be identified. The U-Net receives as input an image patch 302 extracted from the medical image data having voxels labelled with the anatomical objects (resulting from the segmenting performed at step 106). All voxels that do not have an assigned segmentation label are evaluated. The U-Net is fully-convolutional such that I can be applied to patches or regions of arbitrary size. The U-Net outputs a probability map 304 indicating a probability score of voxels belonging to a lymph node. The U-Net models the location of each lymph node in probability map 304 as a Gaussian volume with a size proportional to the lymph node size. Accordingly, voxels will be associated with lower probabilities the further they are from the center of the lymph node. In some embodiments, the probability map 304 may be converted to a binary mask by comparing the probability score to a threshold (e.g., 0.5), such that the binary mask has intensity values of 1 where the lymph node is located and 0 where the lymph node is not located. The voxels of image patch 302 corresponding to the anatomical objects (segmented at step 106) are used to limit evaluation of image patch 302. Specifically, the lymph nodes are identified from voxels of image patch 302 that are not labelled as corresponding to the anatomical objects so that only the possible locations of the lymph nodes are evaluated. The U-Net is trained to map the intensities of image patch 304 as a Gaussian volume representing the location of the lymph node. The U-Net is trained using a negated Dice Coefficient as the loss function between the target t and output x according to Equation 1.

$$\text{Loss} = \frac{-2\sum_i x_i t_i + s}{\sum_i x_i^2 + \sum_i t_i^2 + s}, s = 0.1 \quad \text{(Equation 1)}$$

The loss function of Equation 1 is formulated for each voxel in terms of target value (t), which is the ideal ground truth Gaussian value centered at the lymph node, and the output of the U-Net x at that voxel location. The loss function of Equation 1 performs well on segmentation problems with highly imbalanced classes, which is of particular importance when the objects to be detected comprise such a small fraction of the total image volume, as it is with lymph node detection. Due to the relatively limited amount of data available and the large data requirements to train three dimensional neural networks, the training may be formulated to offset the deficit in training data. In particular, the training may be conducted using a small batch size to facilitate convergence to a less sharp extremum. Further, the training data set may be augmented by, e.g., randomly flipping the individual patches along a randomly chosen axis during training as well as randomly shifting intensity.

The lymph nodes are identified in the medical image data by determining the location of the lymph nodes from probability map 304 through further processing. In one embodiment, locations of lymph nodes are extracted from probability map 304 via non-maximum suppression and scale support filtering. A lymph node location candidate is extracted from probability map 304 if the output at that voxel is a local maxima (non-maxima suppression) and if there is enough support around it to match a Gaussian shape (scale support filtering). As a result, a detected lymph node will have a location (the voxel with a local max probability), a probability value, and a scale estimate (the scale of the best local fitting Gaussian to the probability map).

It should be understood that the present invention is not limited to identification of lymph nodes using a U-Net as described above, and that any other suitable technique for the identifying lymph nodes in medical image data may be employed.

At step 110, the one or more identified lymph nodes are assessed. The lymph nodes may be assessed by applying one or more computer-based automated algorithms. In one embodiment, the lymph nodes are segmented from the medical image data based on the locations of the lymph nodes (identified at step 108). Lymph node segmentation may be performed by applying a U-Net similar to that shown in FIG. 3 (or any other suitable machine learning network). To simplify the segmentation task, only image patches centered at the identified lymph nodes and scaled by the scale estimate determined at step 108 are extracted and input into the U-Net. This will make the segmentation task simpler because all patches will have the lymph node in the center and with an approximately same size. The U-Net is then trained in a supervised manner by using annotated segmentations of the lymph nodes. The segmented lymph nodes are quantified to assess the lymph nodes.

At step 112, the one or more identified lymph nodes and/or the assessment of the one or more identified lymph nodes are output. The identified lymph nodes may be output as a probability map or binary mask. The identified lymph nodes and/or the assessment of the identified lymph nodes can be output by displaying the identified lymph nodes and/or the assessment of the identified lymph nodes on a display device of a computer system, storing the identified lymph nodes and/or the assessment of the identified lymph nodes on a memory or storage of a computer system, or by transmitting the identified lymph nodes and/or the assessment of the identified lymph nodes to a remote computer system.

Embodiments of the present invention were experimentally evaluated using a dataset comprising 390 CT scans having 1519 mediastinal annotations, 589 abdominal annotations, and 910 axillary annotations. Lymph nodes are only present in specific portions of a patient's body and therefore comprise a very small fraction of the total volume of the body. To train a lymph node detector, regions of interest surrounding the lymph nodes were extracted from the scan volumes to allow the detector to focus on learning from these regions of interest. For each lymph node annotation, a cubic patch of size 96 mm is extracted surrounding the annotation location, offset by a random 3D vector with each dimension's magnitude being less than or equal to 24 mm. A 3D U-Net with 3 up sample/down sample levels were used with 64 initial filters and a filter growth rate of 32.

The dataset was split into 85% for training and 15% for testing at the volume level. The split was performed such that the same distribution of lymph nodes for each region is maintained in training and testing. The detected candidates were matched to an annotation only if it lies within the annotation's radius. Any annotation with one or more candidates within its bounds is counted as a successful detection, while any candidate not within the bounds of any annotation is counted as a false positive. Due to their greater clinical significance, only lymph nodes greater than or equal to 1.0 cm in diameter were considered.

Figure 4:
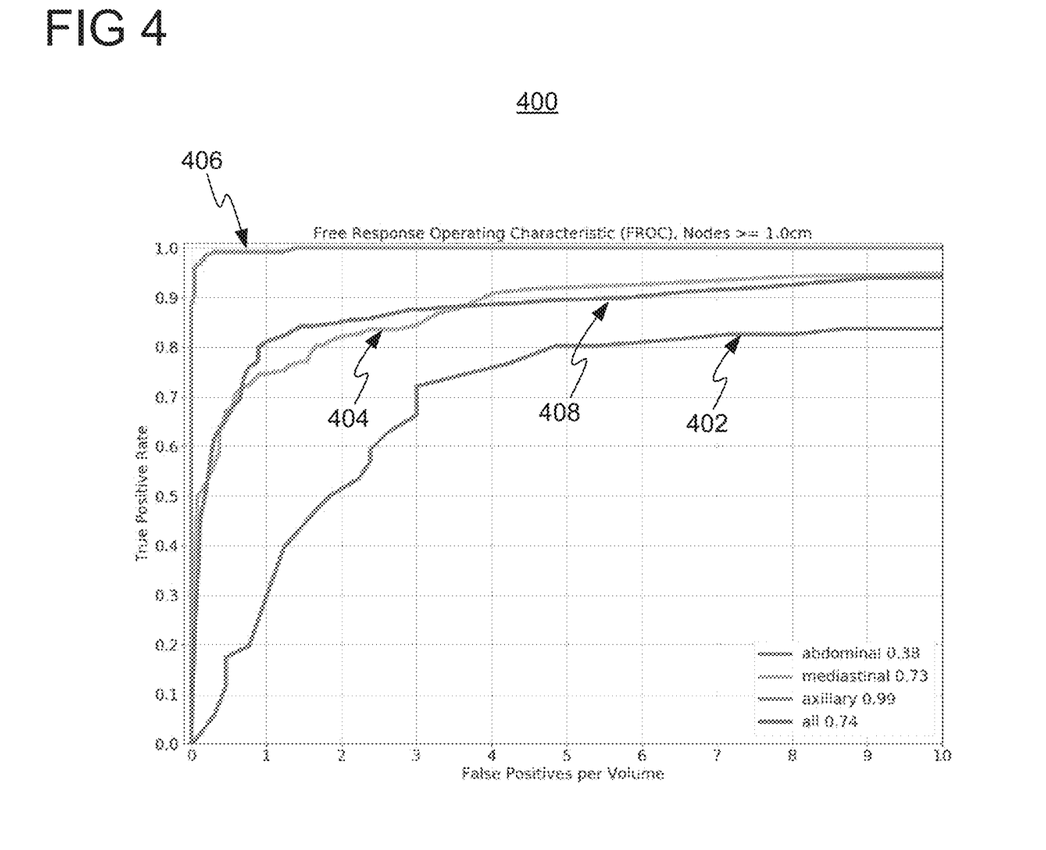
FIG. 4 shows a graph of free-response receiver operating characteristic curves.

The Free-Response Receiver Operating Characteristic (FROC) curve was calculated comparing the true positive rate against the false positives per volume for each node region as well as an overall curve for all node regions. FIG. 4 shows a graph 400 of FROC curves for the abdominal region 402, mediastinal region 404, axillary region 406, and an overall curve for all regions 408. The Y axis represents the true positive rate (TPR) as a percentage and the X axis represents the number of false positives per volume (FP). Exemplary operating points on the curve are: 85% TPR for 1.5 FP overall, 98% TPR for 0.2 FP for axillary nodes, 85% TPR for 3 FP for mediastinal nodes, and 80% TPR with 4.8 FP for abdominal nodes. This performance compares favorably with conventional approaches. For segmentation, a U-Net was trained and evaluated on a subset of 175 CT scans split into 85% for training and 15% for testing. The average Dice coefficient on the test data for the lymph node crop was 0.9.

The lymph node detector showed good performance on axillar and mediastinal nodes. While the abdominal node performance was limited by the lower number of annotations available, the results also showed that lymph node detection in the abdomen region is more challenging.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
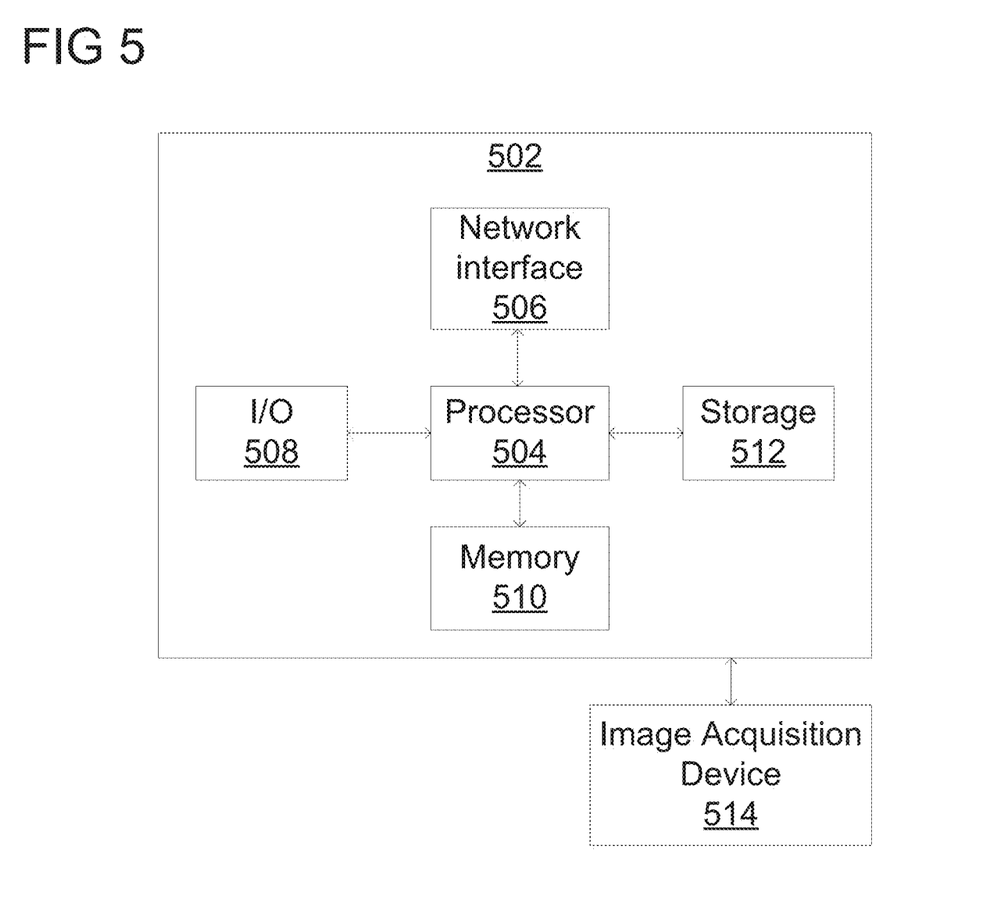
FIG. 5 shows a high-level block diagram of a computer.

A high-level block diagram of an example computer 502 that may be used to implement systems, apparatus, and methods described herein is depicted in FIG. 5. Computer 502 includes a processor 504 operatively coupled to a data storage device 512 and a memory 510. Processor 504 controls the overall operation of computer 502 by executing computer program instructions that define such operations. The computer program instructions may be stored in data storage device 512, or other computer readable medium, and loaded into memory 510 when execution of the computer program instructions is desired. Thus, the method and workflow steps or functions of FIG. 1 can be defined by the computer program instructions stored in memory 510 and/or data storage device 512 and controlled by processor 504 executing the computer program instructions. For example, the computer program instructions can be implemented as computer executable code programmed by one skilled in the art to perform the method and workflow steps or functions of FIG. 1. Accordingly, by executing the computer program instructions, the processor 504 executes the method and workflow steps or functions of FIG. 1. Computer 502 may also include one or more network interfaces 506 for communicating with other devices via a network. Computer 502 may also include one or more input/output devices 508 that enable user interaction with computer 502 (e.g., display, keyboard, mouse, speakers, buttons, etc.).

Processor 504 may include both general and special purpose microprocessors, and may be the sole processor or one of multiple processors of computer 502. Processor 504 may include one or more central processing units (CPUs), for example. Processor 504, data storage device 512, and/or memory 510 may include, be supplemented by, or incorporated in, one or more application-specific integrated circuits (ASICs) and/or one or more field programmable gate arrays (FPGAs).

Data storage device 512 and memory 510 each include a tangible non-transitory computer readable storage medium. Data storage device 512, and memory 510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 508 may include peripherals, such as a printer, scanner, display screen, etc. For example, input/output devices 508 may include a display device such as a cathode ray tube (CRT) or liquid crystal display (LCD) monitor for displaying information to the user, a keyboard, and a pointing device such as a mouse or a trackball by which the user can provide input to computer 502.

An image acquisition device 514 can be connected to the computer 502 to input image data (e.g., medical images) to the computer 502. It is possible to implement the image acquisition device 514 and the computer 502 as one device. It is also possible that the image acquisition device 514 and the computer 502 communicate wirelessly through a network. In a possible embodiment, the computer 502 can be located remotely with respect to the image acquisition device 514.

Any or all of the systems and apparatus discussed herein may be implemented using one or more computers such as computer 502.

One skilled in the art will recognize that an implementation of an actual computer or computer system may have other structures and may contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
receiving medical image data of a patient;
detecting one or more anatomical landmarks in the medical image data;
segmenting one or more anatomical objects from the medical image data based on the one or more detected anatomical landmarks;
identifying one or more lymph nodes in the medical image data based on the one or more detected anatomical landmarks and the one or more segmented anatomical objects using a machine learning network, the machine learning network 1) receiving as input the medical image data having voxels labelled as corresponding to the one or more anatomical objects in accordance with the segmenting, 2) evaluating only voxels of the medical image data that are not labelled as corresponding to the one or more anatomical objects, and 3) generating as output a probability map indicating a probability score of voxels belonging to the one or more lymph nodes to identify the one or more lymph nodes in the voxels that are not labelled as corresponding to the one or more anatomical objects; and
outputting the one or more identified lymph nodes.

2. The method of claim 1, wherein the machine learning network is a U-Net trained to map intensities of voxels of the medical image data as a Gaussian volume.

3. The method of claim 1, further comprising:
assessing the one or more identified lymph nodes.

4. The method of claim 3, wherein assessing the one or more identified lymph nodes comprises:
segmenting the one or more identified lymph nodes from the medical image data; and
quantifying the one or more segmented lymph nodes.

5. The method of claim 1, wherein detecting one or more anatomical landmarks in the medical image data comprises:
detecting the one or more anatomical landmarks in the medical image data using an agent trained with deep reinforcement learning.

6. The method of claim 1, wherein segmenting one or more anatomical objects from the medical image data based on the one or more detected anatomical landmarks comprises:
segmenting the one or more anatomical objects from the medical image data using an adversarial deep image-to-image network.

7. The method of claim 1, wherein the medical image data comprises one or more computed tomography images.

8. An apparatus, comprising:
means for receiving medical image data of a patient;
means for detecting one or more anatomical landmarks in the medical image data;
means for segmenting one or more anatomical objects from the medical image data based on the one or more detected anatomical landmarks;
means for identifying one or more lymph nodes in the medical image data based on the one or more detected anatomical landmarks and the one or more segmented anatomical objects using a machine learning network, the machine learning network 1) receiving as input the medical image data having voxels labelled as corresponding to the one or more anatomical objects in accordance with the segmenting, 2) evaluating only voxels of the medical image data that are not labelled as corresponding to the one or more anatomical objects, and 3) generating as output a probability map indicating a probability score of voxels belonging to the one or more lymph nodes to identify the one or more lymph nodes in the voxels that are not labelled as corresponding to the one or more anatomical objects; and means for outputting the one or more identified lymph nodes.

9. The apparatus of claim 8, wherein the machine learning network is a U-Net trained to map intensities of voxels of the medical image data as a Gaussian volume.

10. The apparatus of claim 8, further comprising:
means for assessing the one or more identified lymph nodes.

11. The apparatus of claim 10, wherein the means for assessing the one or more identified lymph nodes comprises:
means for segmenting the one or more identified lymph nodes from the medical image data; and
means for quantifying the one or more segmented lymph nodes.

12. A non-transitory computer readable medium storing computer program instructions, the computer program instructions when executed by a processor cause the processor to perform operations comprising:
receiving medical image data of a patient;
detecting one or more anatomical landmarks in the medical image data;
segmenting one or more anatomical objects from the medical image data based on the one or more detected anatomical landmarks;
identifying one or more lymph nodes in the medical image data based on the one or more detected anatomical landmarks and the one or more segmented anatomical objects using a machine learning network, the machine learning network 1) receiving as input the medical image data having voxels labelled as corresponding to the one or more anatomical objects in accordance with the segmenting, 2) evaluating only voxels of the medical image data that are not labelled as corresponding to the one or more anatomical objects, and 3) generating as output a probability map indicating a probability score of voxels belonging to the one or more lymph nodes to identify the one or more lymph nodes in the voxels that are not labelled as corresponding to the one or more anatomical objects; and
outputting the one or more identified lymph nodes.

13. The non-transitory computer readable medium of claim 12, wherein detecting one or more anatomical landmarks in the medical image data comprises:
detecting the one or more anatomical landmarks in the medical image data using an agent trained with deep reinforcement learning.

14. The non-transitory computer readable medium of claim 12, wherein segmenting one or more anatomical objects from the medical image data based on the one or more detected anatomical landmarks comprises: segmenting the one or more anatomical objects from the medical image data using an adversarial deep image-to-image network.

* * * * *